US009078559B2

(12) United States Patent
Tsunoda et al.

(10) Patent No.: US 9,078,559 B2
(45) Date of Patent: Jul. 14, 2015

(54) ORAL CAVITY INSERTION INSTRUMENT AND PHARYNGOSCOPE APPARATUS

(75) Inventors: Koichi Tsunoda, Tokyo (JP); Yasushi Tabata, Chiba (JP)

(73) Assignees: Koichi Tsunoda, Tokyo (JP); HOYA CORPORATION, Tokyo (JP)

( * ) Notice: Subject to any disclaimer, the term of this patent is extended or adjusted under 35 U.S.C. 154(b) by 1123 days.

(21) Appl. No.: 12/342,129

(22) Filed: Dec. 23, 2008

(65) Prior Publication Data

US 2009/0171155 A1 Jul. 2, 2009

(30) Foreign Application Priority Data

Dec. 27, 2007 (JP) .................................. 2007-338336

(51) Int. Cl.
| | | |
|---|---|---|
| *A61B 1/32* | (2006.01) | |
| *A61B 1/00* | (2006.01) | |
| *A61B 1/05* | (2006.01) | |
| *A61B 1/06* | (2006.01) | |
| *A61B 1/24* | (2006.01) | |
| *A61B 13/00* | (2006.01) | |

(52) U.S. Cl.
CPC ......... *A61B 1/00052* (2013.01); *A61B 1/00087* (2013.01); *A61B 1/00135* (2013.01); *A61B 1/05* (2013.01); *A61B 1/0676* (2013.01); *A61B 1/0684* (2013.01); *A61B 1/24* (2013.01); *A61B 13/00* (2013.01)

(58) Field of Classification Search
CPC .... A61B 1/267; A61B 1/00052; A61B 1/042; A61B 1/05; A61B 1/24
USPC ........... 128/200.26, 207.14–207.18; 600/200, 600/235–245
See application file for complete search history.

(56) References Cited

U.S. PATENT DOCUMENTS

| 1,613,373 | A | * | 1/1927 | Beck | .............................. | 600/205 |
| 1,638,986 | A | * | 8/1927 | De Zeng | ....................... | 362/139 |
| 2,004,808 | A | * | 6/1935 | Gallasch | ........................ | 600/241 |

(Continued)

FOREIGN PATENT DOCUMENTS

| DE | 8900120 | 2/1990 |
| EP | 0494840 | 7/1992 |

(Continued)

OTHER PUBLICATIONS

English language Abstract of JP 5-176934, Jul. 20, 1993.

(Continued)

*Primary Examiner* — Mary Hoffman
(74) *Attorney, Agent, or Firm* — Greenblum & Bernstein, P.L.C.

(57) ABSTRACT

An oral cavity insertion instrument which is to be attached to a monitor device having a long scope portion is provided. The oral cavity insertion instrument is adapted to be used by being inserted into an oral cavity and has a long cover member having a bore which extends in a longitudinal direction thereof, wherein the scope portion of the monitor is adapted to be inserted into the bore. The oral cavity insertion instrument also has a long tongue depressor in the form of a plate. The tongue depressor is provided adjacent to and in contact with the cover member along the longitudinal direction thereof. The oral cavity insertion instrument includes an attachment unit used to attach the cover member to the monitor device. The tongue depressor includes a tip end having a width greater than that of the cover member. A pharyngoscope apparatus provided with the oral cavity insertion instrument is also provided.

22 Claims, 11 Drawing Sheets

(56) References Cited

U.S. PATENT DOCUMENTS

| | | | | |
|---|---|---|---|---|
| 2,014,879 | A * | 9/1935 | Brooks | 600/248 |
| 2,648,329 | A * | 8/1953 | Morch | 600/193 |
| 2,756,742 | A * | 7/1956 | Barton | 600/205 |
| 3,349,764 | A | 10/1967 | Edinger et al. | |
| 3,435,820 | A | 4/1969 | Taub | |
| 3,734,084 | A * | 5/1973 | Ousterhout | 600/239 |
| 4,742,819 | A * | 5/1988 | George | 600/109 |
| 5,060,633 | A * | 10/1991 | Gibson | 600/193 |
| 5,363,838 | A * | 11/1994 | George | 600/120 |
| 5,513,622 | A * | 5/1996 | Musacchia, Sr. | 124/89 |
| 5,584,796 | A * | 12/1996 | Cohen | 600/201 |
| 5,643,221 | A * | 7/1997 | Bullard | 604/194 |
| 5,845,634 | A * | 12/1998 | Parker | 128/200.26 |
| 5,879,289 | A * | 3/1999 | Yarush et al. | 600/179 |
| 5,941,816 | A * | 8/1999 | Barthel et al. | 600/120 |
| 6,350,235 | B1 * | 2/2002 | Cohen et al. | 600/199 |
| 6,432,046 | B1 * | 8/2002 | Yarush et al. | 600/179 |
| 6,554,765 | B1 * | 4/2003 | Yarush et al. | 600/132 |
| 6,652,453 | B2 * | 11/2003 | Smith et al. | 600/188 |
| 6,655,377 | B2 * | 12/2003 | Pacey | 128/200.26 |
| 6,830,545 | B2 * | 12/2004 | Bendall | 600/114 |
| 6,929,600 | B2 * | 8/2005 | Hill | 600/120 |
| 7,057,639 | B2 * | 6/2006 | Spoonhower et al. | 348/66 |
| D637,715 | S * | 5/2011 | Clarke et al. | D24/137 |
| 2005/0150500 | A1 | 7/2005 | Koyama et al. | |
| 2005/0171399 | A1 * | 8/2005 | Rich et al. | 600/112 |
| 2006/0065268 | A1 | 3/2006 | Koyama et al. | |
| 2007/0106117 | A1 | 5/2007 | Yokota | |
| 2007/0179342 | A1 * | 8/2007 | Miller et al. | 600/188 |
| 2009/0044799 | A1 * | 2/2009 | Qiu | 128/200.26 |

FOREIGN PATENT DOCUMENTS

| | | |
|---|---|---|
| EP | 1 640 033 | 3/2006 |
| GB | 2 431 541 | 4/2007 |
| JP | 3-114201 | 11/1991 |
| JP | 5-176934 | 7/1993 |
| JP | 6-68719 | 9/1994 |
| JP | 2000-175867 | 6/2000 |
| JP | 2007-117116 | 5/2007 |

OTHER PUBLICATIONS

English language Abstract of JP 2000-175867, Jun. 27, 2000.
English translation of Japan Office action, dated Aug. 7, 2012.
Search report from E.P.O., mail date is Oct. 13, 2010.

* cited by examiner

ORAL CAVITY INSERTION INSTRUMENT AND PHARYNGOSCOPE APPARATUS

FIELD OF THE INVENTION

The present invention relates to an oral cavity insertion instrument and a pharyngoscope apparatus provided with the oral cavity insertion instrument.

BACKGROUND ART

When an otorhinolaryngologist, an internist, a pediatrician, or the like views or examines an oropharynx of a patient, a tongue depressor is used to press a tongue of the patient downward to make it easy to view an oral cavity or pharynx of the patient. For example, Japanese laid-open patent publication No. 5-176934 discloses such a tongue depressor.

The tongue depressor disclosed by Japanese laid-open patent publication No. 5-176934 includes a depressor portion and a handle. A physician holds the handle of the tongue depressor and inserts the depressor portion into an oral cavity of a patient. At that time, the physician usually asks the patient to open his/her mouth widely so as to facilitate examination of the oral cavity and pharyngeal cavity. In this state, the physician handles the tongue depressor.

However, if a tongue of a patient is pressed downward in a state such that the patient opens his/her mouth widely, then vomiting reflex is caused to the patient (i.e., the patient retches). Thus, the patient feels uncomfortable. Such patient's experience may be a cause of a psychic trauma. Particularly, infants tend to be uncooperative in subsequent examination or treatment, such as opening of their mouths. The aforementioned uncomfortable experience may cause a trauma to infants, so that they never open their mouths in the presence of a physician after such experience. Furthermore, a patient may close his/her mouth defensively against the vomiting reflex. In such a case, as soon as the physician inserts the tongue depressor into the oral cavity of the patient, the patient close his/her mouth. As a result, examination cannot be completed.

The present invention has been made in view of the above drawbacks. It is, therefore, an object of the present invention to provide an oral cavity insertion instrument and a pharyngoscope apparatus provided with the oral cavity insertion instrument which allow observation of an oral cavity and an oropharynx without causing annoyance.

According to the present invention, there is provided an oral cavity insertion instrument which allows observation of an oral cavity and an oropharynx without causing annoyance. The oral cavity insertion instrument which is to be attached to a monitor device having an elongated (long) scope portion is provided. The oral cavity insertion instrument is adapted to be used by being inserted into an oral cavity and has an elongated (long) cover member having a bore which extends in a longitudinal direction thereof, wherein the scope portion of the monitor is adapted to be inserted into the bore. The oral cavity insertion instrument also has an elongated (long) tongue depressor in the form of a plate. The tongue depressor is provided adjacent to and in contact with the cover member along the longitudinal direction thereof. The oral cavity insertion instrument includes an attachment unit used to attach the cover member to the monitor device. The tongue depressor includes a tip end having a width greater than the width of the cover member.

With the oral cavity insertion instrument having the above configuration, an oral cavity and an oropharynx can be observed without causing annoyance to a subject patient. Particularly, it is possible to effectively prevent vomiting reflex which would be caused by depressing a tongue in a state in which the subject patient opens his/her mouth widely.

The tip end of the tongue depressor may extend beyond a tip end of the cover member in the longitudinal direction. With this configuration, when a tongue is pressed downward (toward a mandible) by the tongue depressor, swelled flesh produced outside the depressed portion can be prevented. Therefore, it is possible to avoid a situation that the view of an image unit of the monitor device is obstructed by the swelled fresh.

The tip end of the tongue depressor may be formed into a rounded shape in a plan view of the tongue depressor. With this configuration, a subject patient can be released from annoyance of pain, and it is possible to avoid a situation that the oral cavity insertion instrument damages a tongue or an oral cavity of the subject patient.

The edge of the tip end of the tongue depressor may be formed into a rounded shape in the thickness direction. With this configuration, a subject patient can be released from annoyance of pain, and it is possible to avoid a situation that the oral cavity insertion instrument damages a tongue or an oral cavity of the subject patient.

The tongue depressor may have a pair of longitudinal side edge portions extending from the cover member in the width direction. With this configuration, when a tongue is pressed downward (toward a mandible) by the tongue depressor, swelled flesh produced outside the depressed portion can be prevented. Therefore, it is possible to avoid a situation that the view of an image unit of the monitor device is obstructed by the swelled fresh.

The edge of each of the longitudinal side edge portions may be formed into a rounded shape in the thickness direction. With this configuration, a subject patient can be released from annoyance of pain, and it is possible to avoid a situation that the oral cavity insertion instrument damages a tongue or an oral cavity of the subject patient.

The tongue depressor may be formed symmetrically with respect to a central axis of the scope portion in a plan view of the tongue depressor. With this configuration, substantially the same forces are applied to both sides of the central axis when a tongue is depressed by the tongue depressor. Thus, the operability of the pharyngoscope apparatus can be improved.

The tongue depressor may have such stiffness as to substantially cause no deformation when a tongue is depressed by the tongue depressor. In this case, a tongue can be depressed with a small force. Thus, burdens on an operator can be reduced.

The cover member may have an approximately constant width over its entire length. In this case, the structure can be simplified. Furthermore, the oral cavity insertion instrument can be smoothly inserted into an oral cavity of a subject patient.

The attachment unit may be formed on a base end of the cover member. With this configuration, the oral cavity insertion instrument can relatively readily be attached to the monitor device.

The attachment unit may include a regulation portion configured to regulate movement of the cover member with respect to the monitor in the longitudinal direction. With this configuration, when the oral cavity insertion instrument is removed from an oral cavity together with the scope portion of the monitor device, the oral cavity insertion instrument is prevented from being detached from the monitor device.

The monitor device may include a joint portion having an engagement pin protruding therefrom. The regulation portion may have an L-shaped engagement portion with which the engagement pin of the joint portion engages. After the scope portion is inserted into the bore of the cover member, the engagement portion is rotated about the central axis of the scope portion. Thus, the engagement pin engages with the engagement portion, thereby regulating movement of the cover member with respect to the joint portion in the longitudinal direction. With this configuration, the structure of regulation portion can be simplified. The oral cavity insertion instrument can be readily attached (or fixed) to the monitor device.

According to another aspect of the present invention, there is provided a pharyngoscope apparatus which allows observation of an oral cavity and an oropharynx without causing annoyance to a patient. The pharyngoscope apparatus has the aforementioned oral cavity insertion instrument and a monitor device including a scope portion in the form of a rod shape extending in a longitudinal direction.

With the pharyngoscope apparatus having the above configuration, an oral cavity and an oropharynx can be observed without causing annoyance to a subject patient. Particularly, it is possible to effectively prevent vomiting reflex which would be caused by depressing a tongue in a state in which a subject patient opens his/her mouth widely.

The monitor device may include a monitor device body connected to a base end of the scope portion, an image unit operable to obtain an image of an observation area in the oral cavity, and a display unit having a display surface, and the display unit provided on the monitor device body for displaying an image taken by the image unit on the display surface. With this configuration, an image to be observed can be viewed on the display unit. Thus, the operability of the pharyngoscope apparatus can be improved.

The monitor device may include an illumination unit operable to illuminate the observation area of which image is to be taken by the image unit. With this configuration, an inside of the oral cavity can be illuminated. Thus, a clear image can be provided by an image pickup device. Furthermore, a subject patient can close his/her mouth while an operator observes his/her oral cavity or oropharynx. Thus, burdens on the subject patient can be reduced.

The image unit may include an object lens provided at a tip end portion of the scope portion and an image pickup device having a light-receiving surface on which an image of the observation area is focused by the object lens. The illumination unit may include a pair of illumination portions provided at the tip end portion of the scope portion so as to be symmetric with respect to the object lens of the image unit. With this configuration, illumination light can be applied uniformly to the entire observing area.

The illumination portions may be located on a line parallel to the width direction of the tongue depressor. With this configuration, the illumination unit can illuminate an increased area of an oral cavity.

The display unit may be disposed such that the central axis of the scope portion intersects the display unit. With this configuration, the apparatus can be reduced in size.

The central axis of the scope portion may intersect the display surface of the display unit. With this configuration, the visibility of the display surface in the display unit can be improved during use of the pharyngoscope apparatus (when an operator observes an oral cavity or oropharynx).

The display surface of the display unit may be inclined with respect to the central axis of the scope portion. With this configuration, the visibility of the display unit can be improved.

The monitor device may have a shading portion provided on the monitor device body so as to surround a periphery of the display unit. With this configuration, a portion of external light can be properly prevented from entering the display unit, thereby improving the visibility of the display unit.

The monitor device body may include at least one finger placing portion on which a finger of an operator can be placed to hold the monitor device body. With this configuration, an operator can readily hold the pharyngoscope apparatus. Thus, burdens on the operator can be reduced.

The finger placing portion may be formed by a protrusion formed at an end of the monitor device body near the scope portion. With this configuration, the structure of the finger placing portion can be simplified.

The finger placing portion may be formed by a concave portion formed on the monitor device body. With this configuration, the structure of the finger placing portion can be simplified.

The monitor device body may include a first finger placing portion formed on a first surface of the monitor device body and a second finger placing portion including a concave portion formed on a second surface located at the opposite side of the first surface of the monitor device body. The first finger placing portion may include a protrusion formed at an end of the first surface of the monitor device body near the scope portion. With this configuration, a little finger can be placed on the first finger placing portion, and an index finger, a middle finger, or a ring finger can be placed on the second finger placing portion. Accordingly, the pharyngoscope apparatus can be held remarkably readily.

According to the present invention, an oral cavity and an oropharynx can be observed without necessity for a subject patient to open his/her mouth widely, or an oral cavity and an oropharynx can be observed even if a subject patient closes his/her mouth. Therefore, observation of an oral cavity and an oropharynx can be conducted without causing annoyance to a subject (e.g., patient). Particularly, according to the present invention, it is possible to effectively prevent vomiting reflex which would be caused by depressing a tongue in a state in which a subject patient opens his/her mouth widely.

Furthermore, according to the present invention, an operator can observe an oral cavity and an oropharynx with an image taken by the image unit. Therefore, an oral cavity and an oropharynx can be observed with an increased area as compared to a conventional technique in which an operator (e.g., a physician) directly sees an oral cavity and an oropharynx. Thus, the oral cavity and the oropharynx can be observed with accuracy.

In a conventional case in which an operator directly sees an oral cavity and an oropharynx, the operator has to change his/her posture or line of sight to accurately observe the oral cavity and the oropharynx. In contrast, according to the present invention, an operator can maintain his/her posture or line of sight to be constant because the operator can observe an oral cavity and an oropharynx with an image taken by the image unit. Accordingly, physical burdens on the operator can be reduced.

The above and other objects, features, and advantages of the present invention will be apparent from the following description when taken in conjunction with the accompanying drawings which illustrate preferred embodiments of the present invention by way of example.

DETAILED DESCRIPTION OF THE PREFERRED EMBODIMENTS

A pharyngoscope apparatus including an oral cavity insertion instrument according to preferred embodiments of the present invention will be described below with reference to FIGS. 1 to 11D.

First, a pharyngoscope apparatus according to a preferred embodiment of the present invention will be described below. The pharyngoscope apparatus has an attachable oral cavity insertion instrument according to the present invention.

Figure 1:
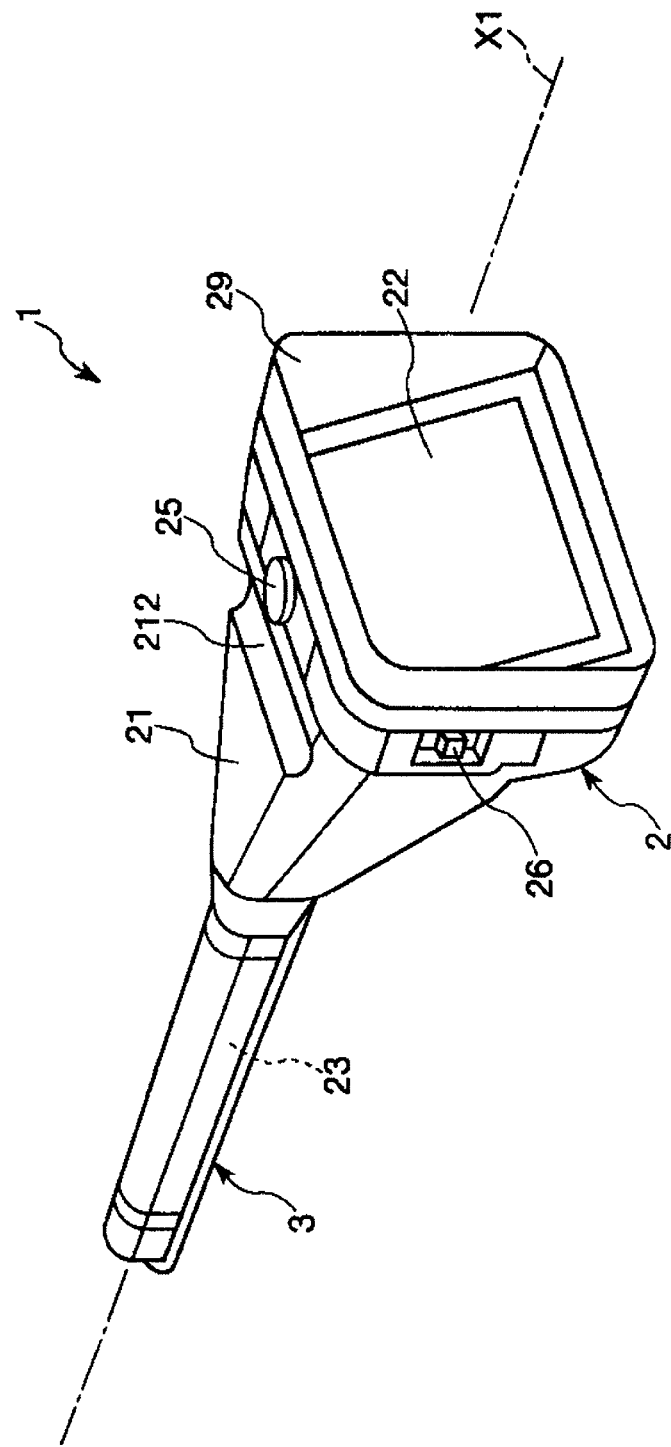
FIG. 1 is a perspective view schematically showing a preferred embodiment of a pharyngoscope apparatus according to the present invention.
Figure 2:
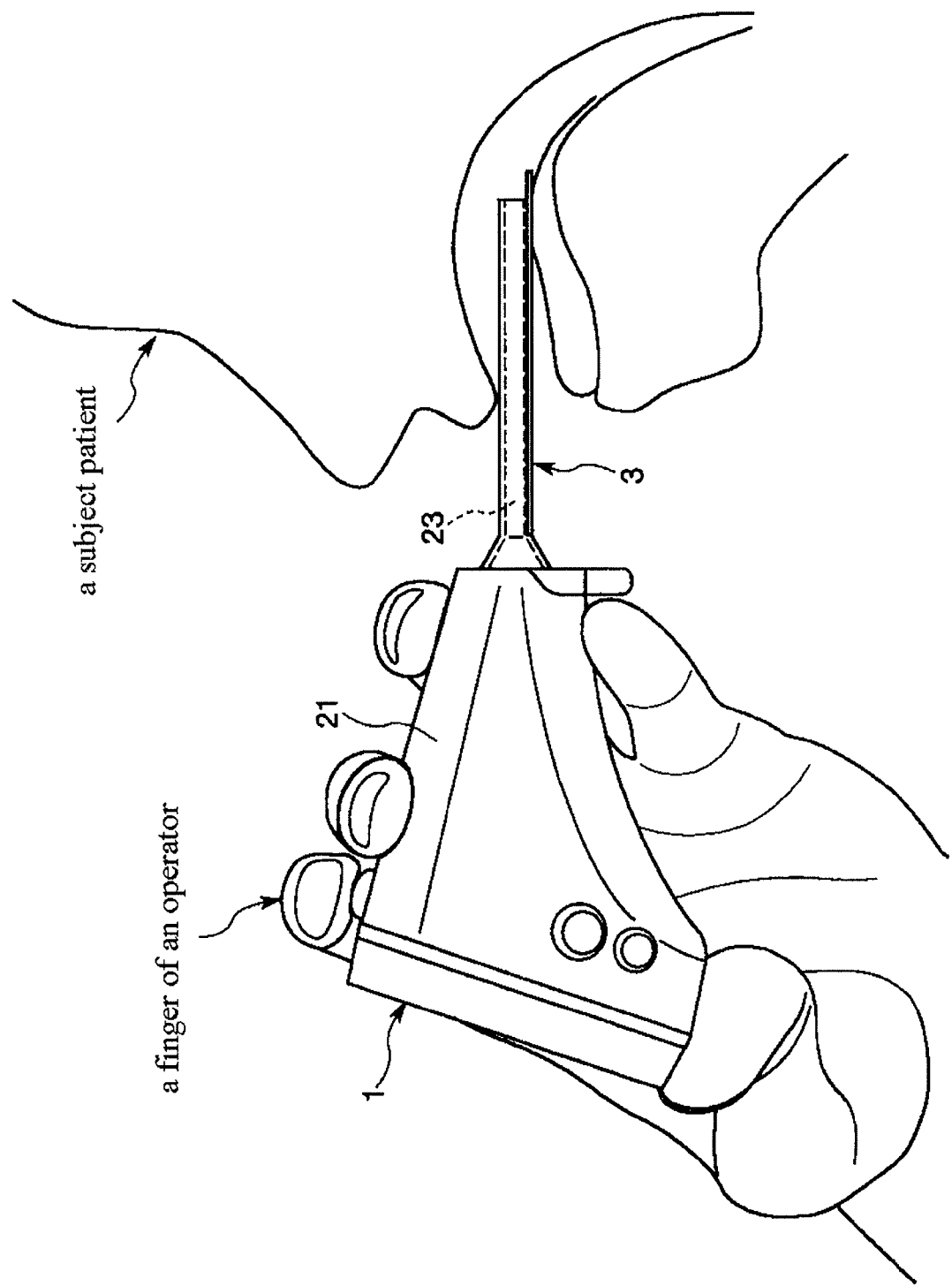
FIG. 2 is a schematic diagram showing an example of use of the pharyngoscope apparatus shown in FIG. 1.
Figure 3:
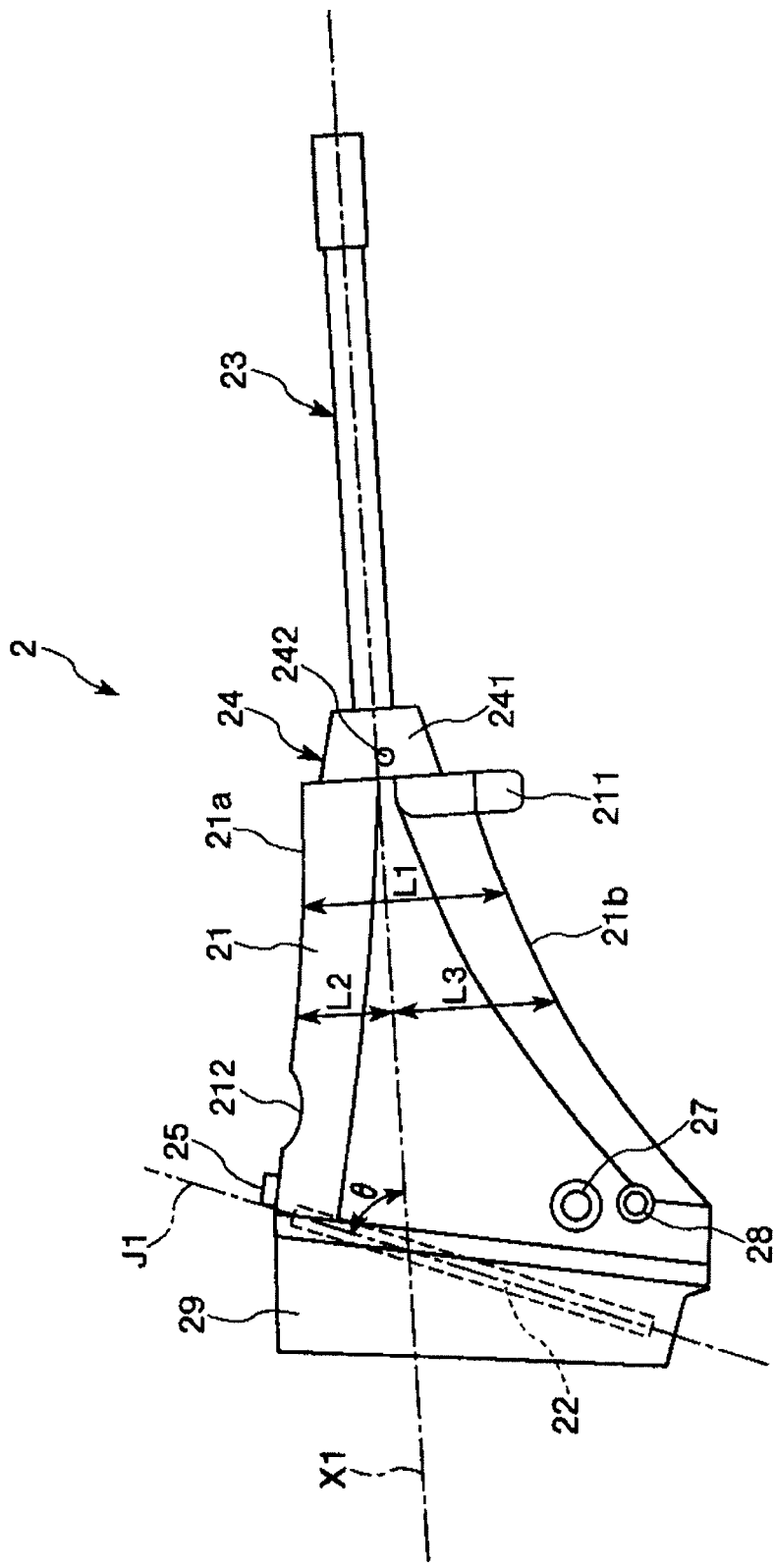
FIG. 3 is a side view schematically showing a monitor device of the pharyngoscope apparatus shown in FIG. 1.
Figure 4:
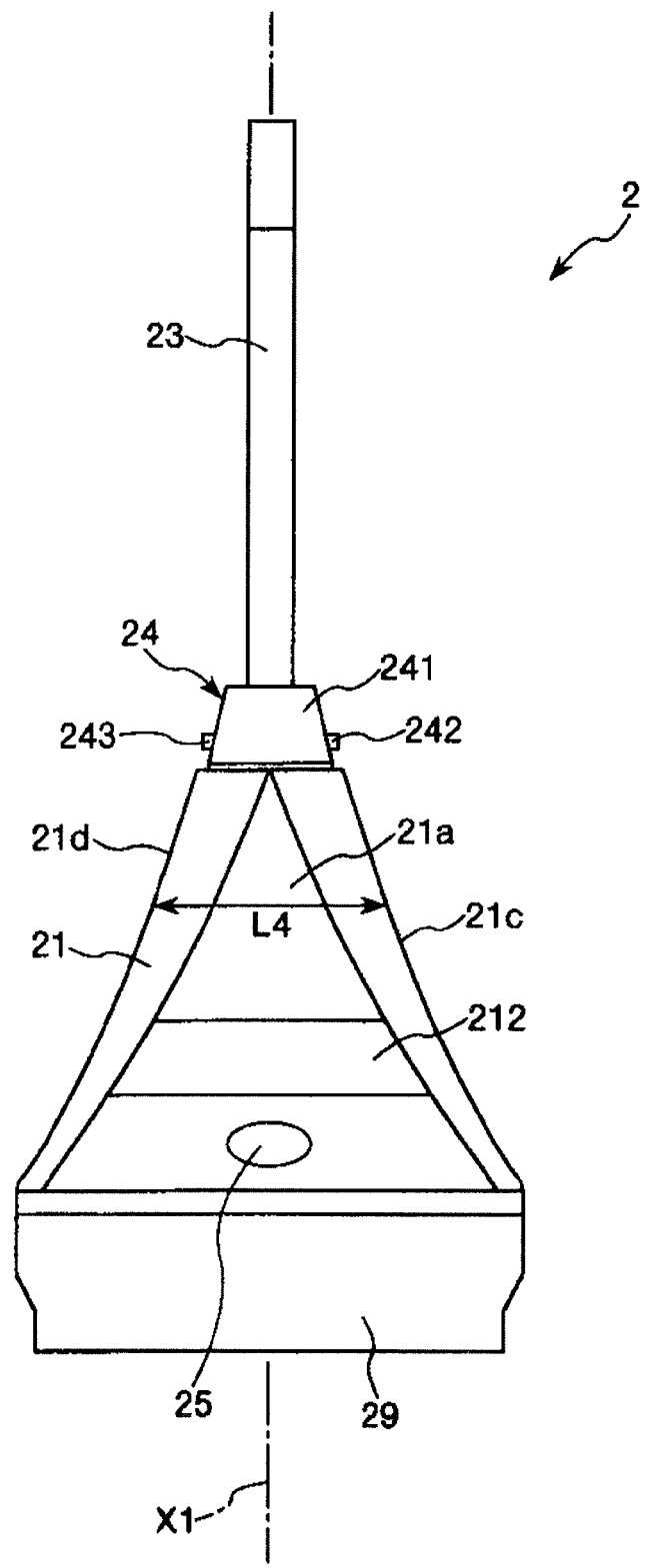
FIG. 4 is a plane view schematically showing the monitor device shown in FIG. 3.
Figure 5:
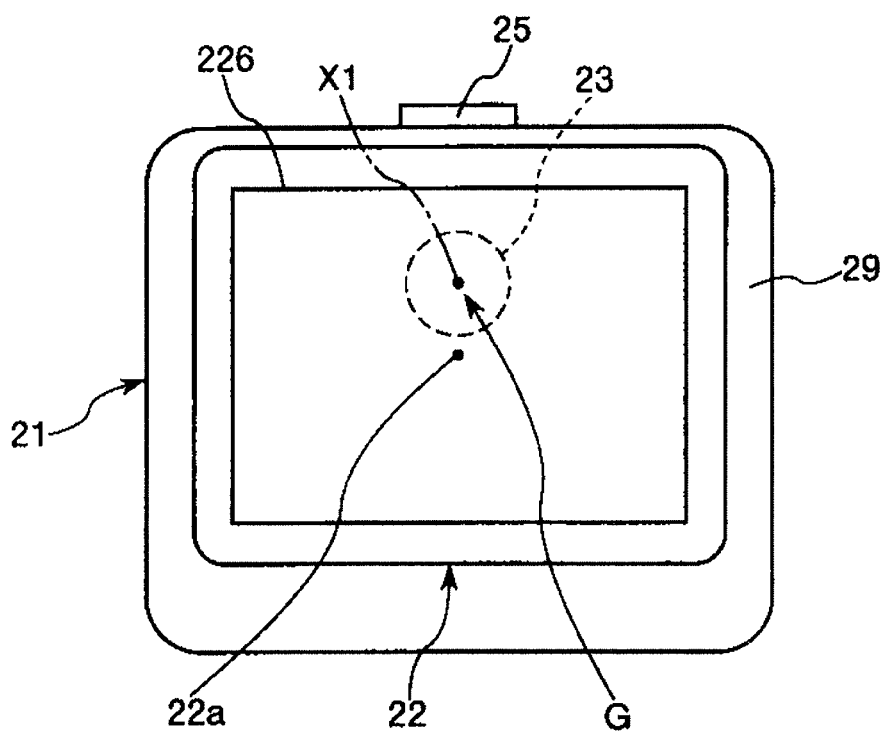
FIG. 5 is a rear view schematically showing the monitor device shown in FIG. 3.
Figure 6:
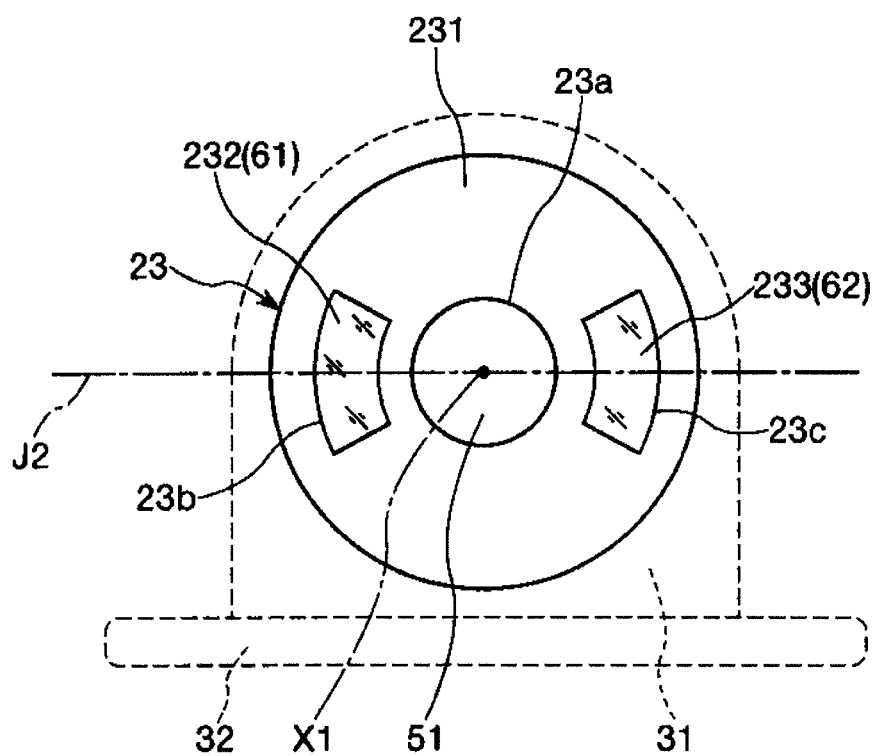
FIG. 6 is a front view schematically showing a tip end portion of a scope portion in the monitor device shown in FIG. 3.
Figure 7:
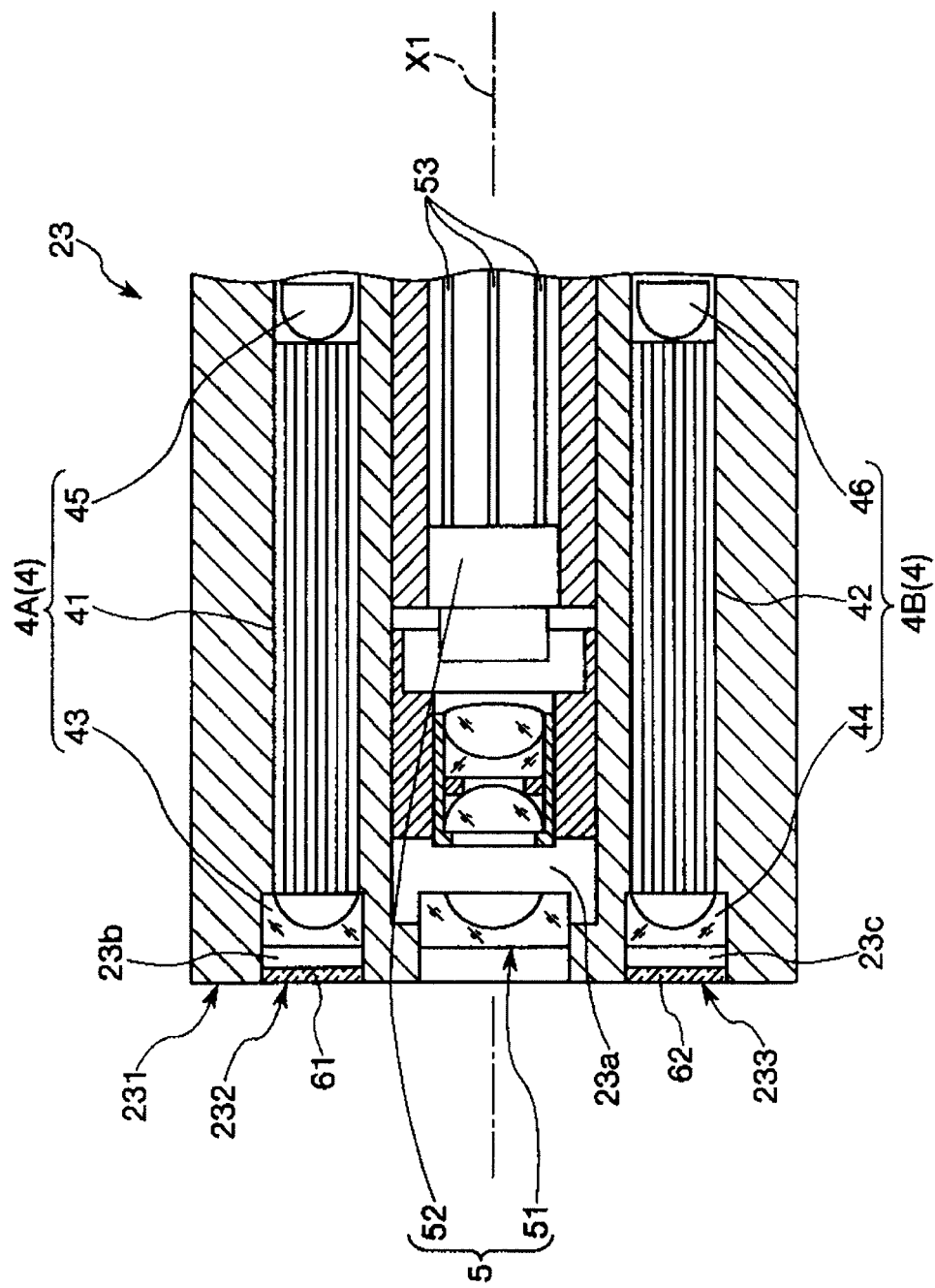
FIG. 7 is a cross-sectional view schematically showing the tip end portion of the scope portion shown in FIG. 6.
Figure 8:
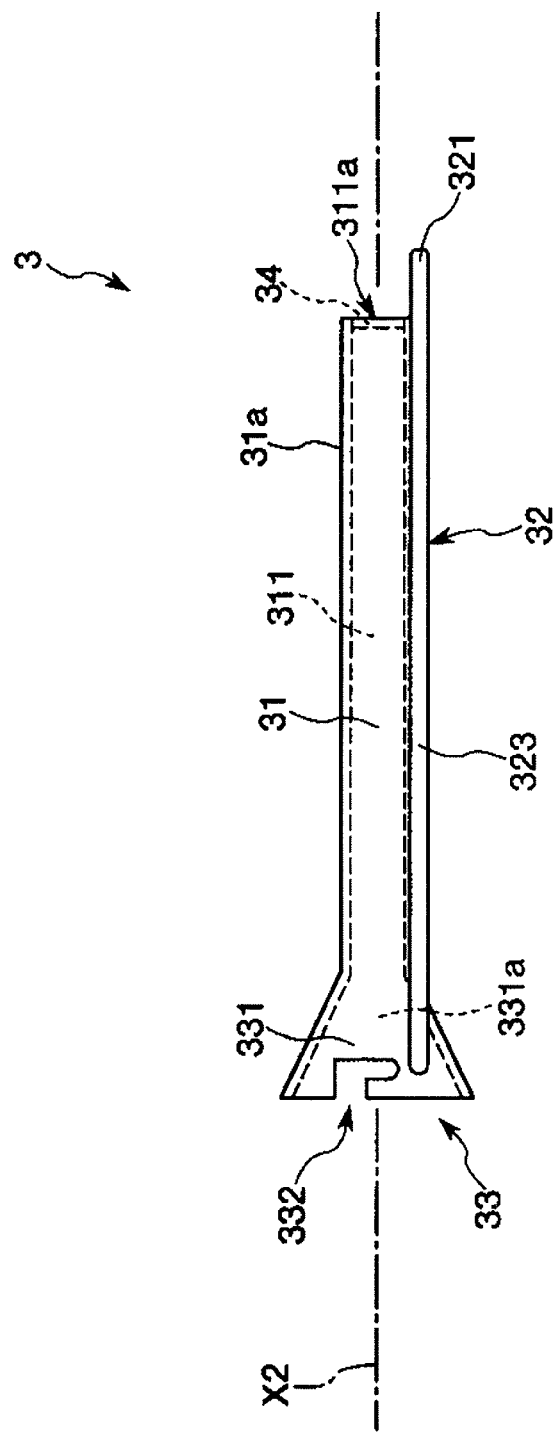
FIG. 8 is a side view schematically showing an oral cavity insertion instrument of the pharyngoscope apparatus shown in FIG. 1.
Figure 9:
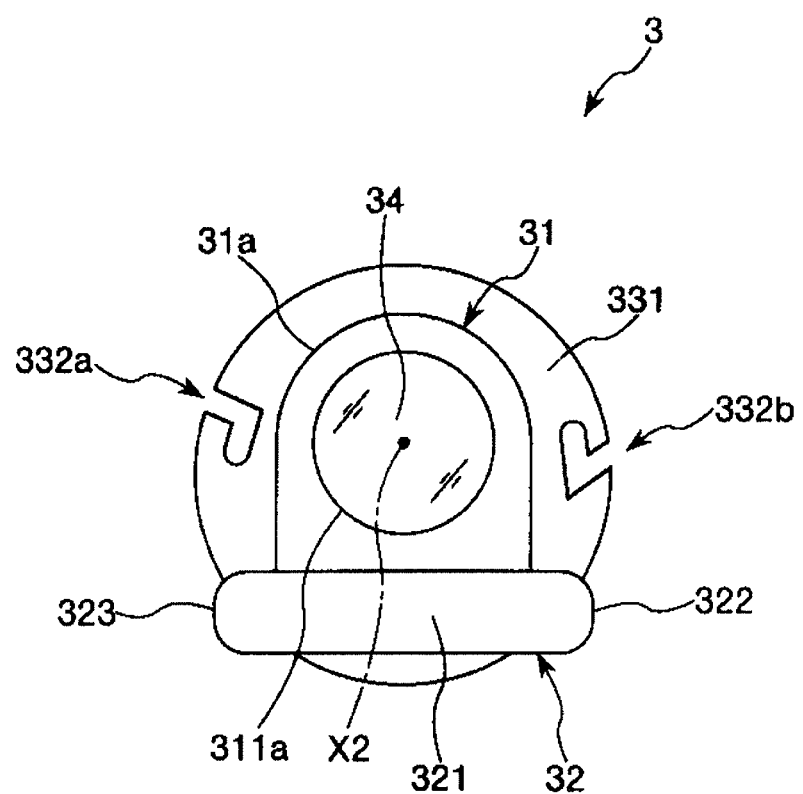
FIG. 9 is a front view schematically showing the oral cavity insertion instrument shown in FIG. 8.
Figure 10:
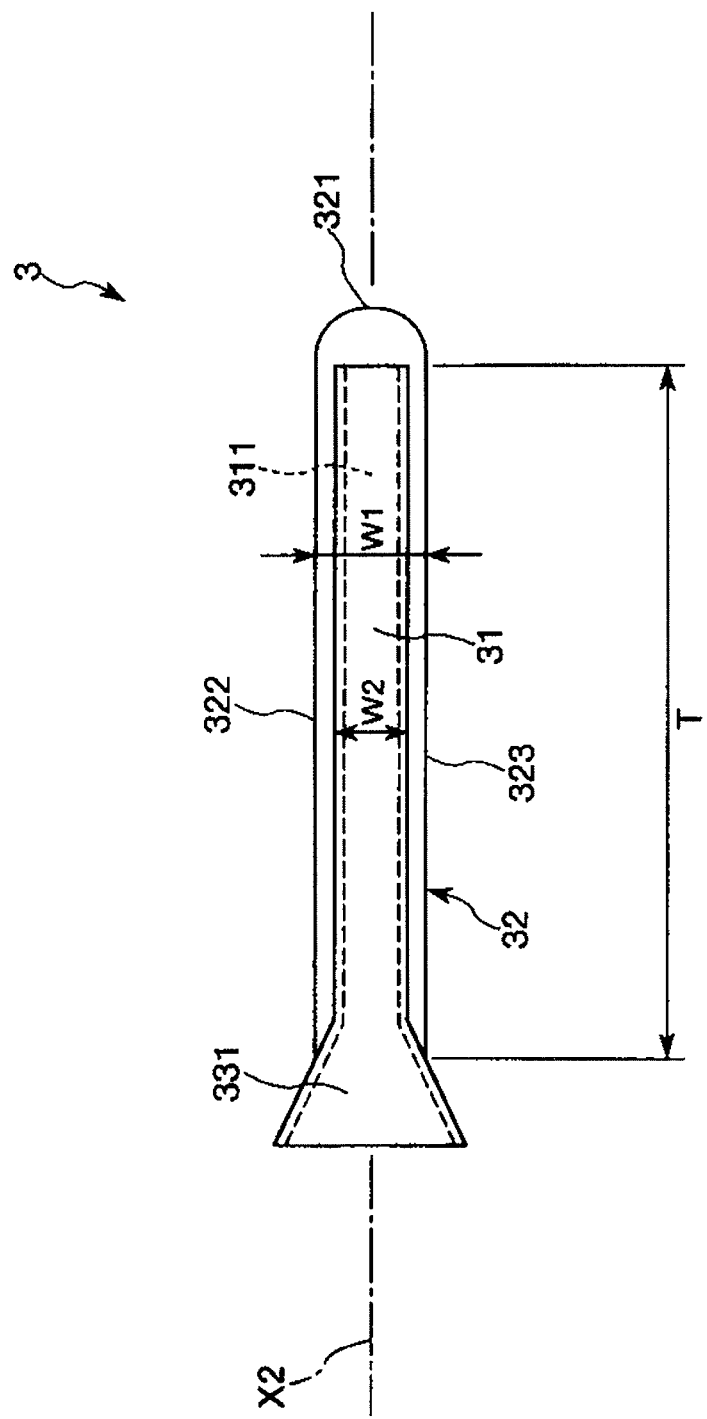
FIG. 10 is a plane view schematically showing the oral cavity insertion instrument shown in FIG. 8.
Figure 11:
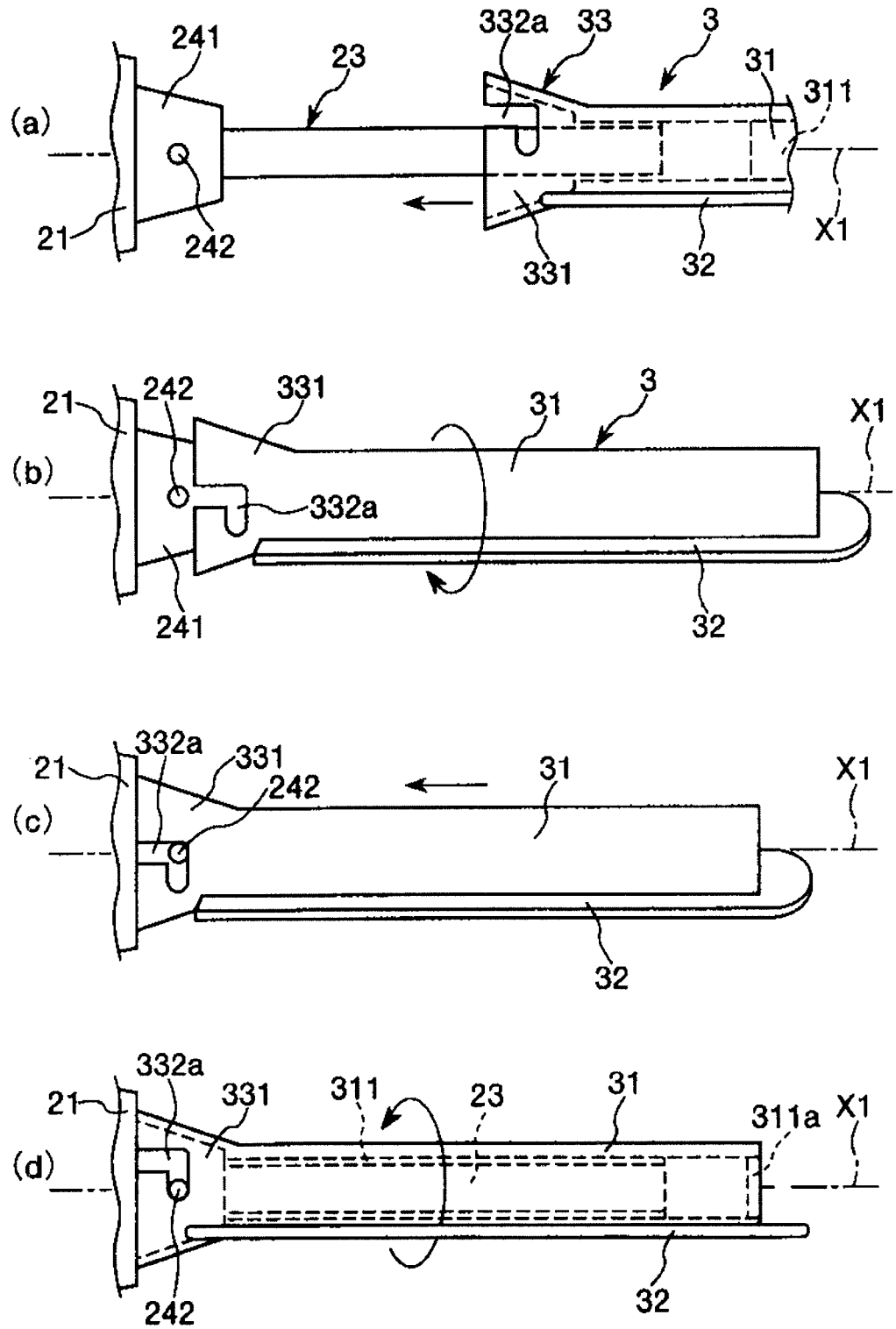
FIGS. 11A to 11D are schematic views showing processes of attachment of the oral cavity insertion instrument to the monitor device.

FIG. 1 is a perspective view schematically showing a preferred embodiment of a pharyngoscope apparatus 1 according to the present invention. FIG. 2 is a schematic diagram showing an example of use of the pharyngoscope apparatus 1 shown in FIG. 1. FIG. 3 is a side view schematically showing a monitor device 2 of the pharyngoscope apparatus 1 shown in FIG. 1. FIG. 4 is a plane (top) view schematically showing the monitor device 2. FIG. 5 is a rear view schematically showing the monitor device 2. FIG. 6 is a front view schematically showing a tip end portion of a scope portion 23 in the monitor device 2. FIG. 7 is a cross-sectional view schematically showing the tip end portion of the scope portion 23. FIG. 8 is a side view schematically showing an oral cavity insertion instrument 3 of the pharyngoscope apparatus 1. FIG. 9 is a front view schematically showing the oral cavity insertion instrument 3. FIG. 10 is a plane (top) view schematically showing the oral cavity insertion instrument 3. FIGS. 11A to 11D are schematic views showing the processes of attachment of the oral cavity insertion instrument 3 to the monitor device 2. For convenience of explanation, upper, lower, right, and left sides in FIGS. 3 to 5, 8, and 9 will be referred to as "upper," "lower," "right," and "left," respectively, in the following description.

As shown in FIG. 1, the pharyngoscope apparatus 1 includes a monitor device 2 and an oral cavity insertion instrument 3 attachable to the monitor device 2.

As shown in FIG. 3, the monitor device 2 includes a monitor device body 21, a display unit (monitor) 22 provided on the monitor device body 21, a scope portion 23 extending in a longitudinal direction from the monitor device body 21, and a joint portion 24 to which the oral cavity insertion instrument 3 is attached. As shown in FIG. 7, the scope portion 23 includes an illumination unit 4 and an image unit 5 therein. In the present embodiment, the scope portion 23 is formed by a hard elongated (long) member (cylindrical member) extending in the longitudinal direction. The scope portion 23 may be formed by a flexible elongated member.

As shown in FIG. 8, the oral cavity insertion instrument 3 has a cover member 31 to which the scope portion 23 of the monitor device 2 is inserted, a tongue depressor 32 provided below the cover member 31 in a state that the tongue depressor 32 is adjacent to and in contact with the cover member 31, and an attachment unit 33 used to attach the cover member 31 to the joint portion 24 of the monitor device 2.

The pharyngoscope apparatus 1 is used as shown in FIG. 2. Specifically, the oral cavity insertion instrument 3 is attached (fixed) to the monitor device 2 so as to cover the scope portion 23. The oral cavity insertion instrument 3 attached to the monitor device 2 is inserted into an oral cavity of a subject (patient). While a tongue of the subject patient is being pressed downward (toward a mandible) by the oral cavity insertion instrument 3, an image of the oral cavity and oropharynx is taken by the image unit 5 provided in the scope portion 23. The image taken by the image unit 5 is displayed on the display unit 22.

The structures of the monitor device 2 and the oral cavity insertion instrument 3 will be described below in detail.

As shown in FIG. 3, the entire monitor device body 21 is of a quadrangular pyramid shape. The display unit 22 is provided at a location corresponding to a base of the quadrangular pyramid. The joint portion 24 and the elongated (cylindrical) scope portion 23 are provided at a location corresponding to a vertex of the quadrangular pyramid.

The monitor device body 21 has an upper surface 21a and a lower surface 21b. In FIG. 3, L1 denotes a distance between the upper surface 21a and the lower surface 21b, L2 a distance between the central axis X1 of the scope portion 23 and the upper surface 21a, and L3 a distance between the central axis X1 of the scope portion 23 and the lower surface 21b. The distance L1 gradually increases from the scope portion 23 toward the display unit 22. The difference (L3−L2) between the distance L2 and the distance L3 at the same point on the central axis X1 gradually increases from the scope portion 23 toward the display unit 22.

Furthermore, the upper surface 21a and the lower surface 21b of the monitor device body 21 are slightly curved respectively so as to increase the distance L1. Specifically, the upper surface 21a is slightly curved upward in FIG. 3, and the lower surface 21b is slightly curved downward in FIG. 3.

With this configuration of the upper surface 21a and the lower surface 21b of the monitor device body 21, the monitor device body 21 can easily fit in an operator's hand. Therefore, the operator can readily hold the monitor device body 21 (or the monitor device 2).

Furthermore, the monitor device body 21 has a first finger placing portion 211 formed on the lower surface 21b for placing an operator's little finger thereon. The first finger placing portion 211 is located at an end of the lower surface of the monitor device body 21 near the scope portion 23. The first finger placing portion 211 is formed by a protrusion extending downward in FIG. 3. As shown in FIG. 2, an operator can firmly hold the monitor device body 21 with a small force by placing or engaging his/her little finger with the first finger placing portion 211.

Additionally, the monitor device body 21 has a second finger placing portion 212 formed on the upper surface 21a for placing an operator's middle finger thereon. The second finger placing portion 212 is formed by a groove (or a concave portion) extending in a direction perpendicular to the central axis X1. The groove (or the second finger placing portion 212) opens at its opposite ends. The groove has a curved cross-section as shown in FIG. 3. As shown in FIG. 2, an operator can firmly hold the monitor device body 21 with a small force by placing or engaging his/her middle finger with the second finger placing portion 212.

Thus, the first finger placing portion 211 and the second finger placing portion 212 are provided on the monitor device body 21 in the present embodiment. Those finger placing portions allow an operator to firmly hold the monitor device body 21 with a small force. Accordingly, the position of the monitor device 2 (the pharyngoscope apparatus 1) can be stabilized, and the operability of the pharyngoscope apparatus 1 can be improved.

Moreover, the monitor device body 21 has a power button 25 formed on the upper surface 21a thereof. The power button 25 is located at a position closer to the monitor 22 than the second finger placing portion 212. The power button 25 is configured such that an operator can operate the power button 25 with his/her index finger. With this configuration, while holding the monitor device body 21 as described above, an operator can readily operate the power button 25 with his/her index finger of the hand holding the monitor device body 21.

The monitor device 2 is turned on and off by operation of the power button 25. When the monitor device 2 is turned on, electric power is supplied to each part of the monitor device 2 including the display unit 22, the image unit 5, and the illumination unit 4. At that time, an image taken by the image unit 5 is displayed on a display surface of the display unit 22.

As shown in FIG. 4, the monitor device body 21 is configured so as to be symmetric with respect to the central axis X1. Therefore, the operability of the pharyngoscope apparatus 1 can be improved for both of a right-handed operator and a left-handed operator.

In FIG. 4, L4 denotes a distance between a rightward side surface 21c and a leftward side surface 21d. The distance L4 gradually increases from the scope portion 23 toward the monitor 22. With this configuration, an operator can readily hold the monitor device body 21.

As shown in FIG. 1, the monitor device body 21 has a sliding lever 26 provided on the side surface 21d. The sliding lever 26 is used to open and close a battery cover for loading a battery as a power source to the monitor device 2.

As shown in FIG. 3, the monitor device body 21 has an external power source terminal 27 and an output terminal 28 provided on the side surface 21c. The external power source terminal 27 is used to connect the monitor device 2 to an external power source when the external power source is used instead of the internal battery. The output terminal 28 is used to connect the monitor device 2 to an external device other than the display unit 22, such as a television or a PC monitor, when an image taken by the image unit 5 is displayed on the external device.

As shown in FIG. 1, the monitor device 2 has a shading portion 29 provided on the monitor device body 21 so as to surround a periphery of the display unit 22. The shading portion 29 is in the form of a frame. With the shading portion 29, external light can be properly prevented from entering the display surface of the display unit 22, thereby improving the visibility of the display surface in the display unit 22.

Constituent material of the monitor device body 21 is not limited to a specific one. For example, various polymeric materials such as polycarbonate may be used for the monitor device body 21.

Constituent material for the shading portion 29 is not limited to a specific one. In addition to the materials described in connection with the monitor device body 21, rubber materials, such as natural rubber (NR), styrene-butadiene rubber (SBR), silicon rubber, acrylic rubber, and isoprene rubber, and various types of elastomer, such as polyurethane thermoplastic elastomer and polyester thermoplastic elastomer, may be used for constituent material of the shading portion 29. Particularly, rubber materials are advantageous in that the shading portion 29 can be improved in resistance to dropping and impact.

As shown in FIG. 5, the central axis X1 of the scope portion 23 intersects the display surface of the display unit 22. With this configuration, the size of the monitor device 2 can be reduced.

Additionally, in the present embodiment, the central axis X1 intersects the display surface of the display unit 22 at a point G, which is deviated upward from the center 22a of the display unit 22. With this configuration, the visibility of the display surface in the display unit 22 can be improved during use of the pharyngoscope apparatus 1 (when an operator observes an oral cavity or oropharynx).

Furthermore, as shown in FIG. 3, the display surface of the display unit 22 is inclined with respect to the central axis X1 of the scope portion 23 such that the display surface faces slightly upward. With this configuration, the visibility of the display unit 22 can be further improved during use of the pharyngoscope apparatus 1. It is preferable that an angle $\theta$ between the central axis X1 of the scope portion 23 and the display surface of the display unit 22 (as shown by chain line J1 in FIG. 3) be in a range of from 50° to 80°, more preferably be about 65°. Within such a range of the angle $\theta$, the aforementioned advantage becomes significant.

As shown in FIG. 3, the joint portion 24 includes a base portion 241 in the form of a circular truncated cone and a pair of engagement pins 242 and 243 protruding radially outward from the base portion 241. The engagement pins 242 and 243 are provided symmetrically with respect to the central axis X1.

The scope portion 23 is in the form of an elongated cylinder (rod). Since the scope portion 23 is inserted into an oral cavity of a subject patient in a state that it is inserted into the bore of the cover member 31, the scope portion 23 is configured to be long enough to reach a deep inner space of an oral cavity.

As shown in FIGS. 6 and 7, three bores 23a, 23b, and 23c are formed in the scope portion 23. Those bores 23a, 23b, and 23c extend in parallel to the central axis X1 and open at a tip end portion 231 of the scope portion 23. As shown in FIG. 6, the bore 23a is located at a central portion of the tip end portion 231. The bores 23b and 23c are located symmetrically with respect to the bore 23a. The bores 23a, 23b, and 23c are located on line J2 extending in parallel to the width direction of the tongue depressor 32, i.e., extending in a direction that is parallel to the width direction of the tongue depressor 32 and is perpendicular to the central axis X1.

An object lens system 51 is fitted into the bore 23a. Substantially colorless and transparent members 61 and 62 are fitted into the bores 23b and 23c, respectively. For example, those colorless and transparent members 61 and 62 are formed of various glass materials or various resin materials. The colorless and transparent members 61 and 62 form illumination windows 232 and 233.

As shown in FIG. 7, the illumination unit 4 includes a first illumination portion 4A and a second illumination portion 4B. Those illumination portions 4A have the same structure. Specifically, the first illumination portion 4A includes a planoconcave lens 43 disposed within the bore 23b, an optical fiber bundle 41, and an LED 45. The second illumination portion 4B also includes a planoconcave lens 44, an optical fiber bundle 42, and an LED 46. The following description is focused on the first illumination portion 4A only, and the detailed explanation for the second illumination portion 4B will be omitted from the description.

The optical fiber bundle 41 is provided along a longitudinal direction of the bore 23. The planoconcave lens 43 and the LED 45 are provided on a tip end and a base end of the optical fiber bundle 41, respectively. The planoconcave lens 43 is disposed near the illumination window 232 so as to face the illumination window 232.

When the LED 45 emits light, the light comes from the tip end of the optical fiber bundle 41. The outgoing light passes through the planoconcave lens 43. Then, through the illumination window 232, the outgoing light illuminates an area (or an object) to be observed. When the outgoing light passes through the planoconcave lens 43, it is diverged and uniformized. As a result, the monitor device 2 can illuminate the observing area uniformly with a wide range.

The LEDs 45 and 46 may be disposed adjacent to the planoconcave lenses 43 and 44 so that light emitted from the LEDs 45 and 46 is introduced directly to the planoconcave lenses. In such a case, the optical fiber bundles 41 and 42 may not be provided in the scope portion 23.

With the illumination unit 4 thus arranged, when an operator observes an oral cavity of a subject patient, an image of an observing area can be reliably taken by the image unit 5 without introducing external light from the outside of the oral cavity, such as daylight or light of a penlight. Accordingly, the subject patient can close his/her mouth while an operator observes his/her oral cavity. Thus, burdens on the subject patient can be reduced.

Furthermore, the first illumination portion 4A and the second illumination portion 4B are provided symmetrically with respect to the object lens system 51. Therefore, the illumination unit 4 can illuminate an observing area more uniformly, and the image unit 5 can take an image of the observing area more clearly.

Moreover, both of the first illumination portion 4A and the second illumination portion 4B are located on the line J2. Therefore, a portion of outgoing light emitted from the first and second illumination portions 4A and 4B can be effectively prevented from being shielded by a tip end 321 of the tongue depressor 32 (see FIG. 8). Thus, the illumination unit 4 can illuminate an increased area of an oral cavity.

As shown in FIG. 7, the image unit 5 includes the aforementioned object lens system (optical system) 51 and an image pickup device 52 such as a CCD image sensor or a C-MOS sensor. The image pickup device 52 is located closer to the base end of the scope portion 23 than the object lens system 51. The object lens system 51 and the image pickup device 52 are provided within the bore 23a of the scope portion 23. The image pickup device 52 is connected to signal lines 53 extending through the bore 23a.

The illumination light emitted from the illumination unit 4 reflects from an observing area to produce reflection light, which forms an image of the observing area. A portion of the reflection light is introduced into the object lens system 51 and focused on a light-receiving surface of the image pickup device 52.

The image pickup device 52 receives the reflection light focused on the light-receiving surface. As a result, the image of the observing area is obtained. The image pickup device 52 outputs image signals (e.g., CCD signals) corresponding to the image of the observing area taken. The image signals are inputted to a signal processing circuit (not shown) via the signal lines 53. The signal processing circuit conducts predetermined signal processing on the image signals. The image signals subjected to the signal processing are converted into predetermined television signals and then inputted to the display unit 22. Consequently, the image (electronic image) of the observing area obtained by the image pickup device 52 is displayed on the display surface of the display unit 22.

According to the illumination unit 4 and the image unit 5 as described above, an oral cavity and an oropharynx can be observed without necessity for a subject patient to open his/her mouth widely. The oral cavity insertion instrument 3 can be inserted into a mouth opened narrowly. Therefore, observation can be conducted even if a subject patient closes his/her mouth after the oral cavity insertion instrument 3 has been inserted to his/her mouth. As a result, burdens on the subject patient can be reduced. Particularly, it is possible to effectively prevent vomiting reflex which would be caused by depressing a tongue in a state in which a subject patient opens his/her mouth widely.

Next, the detail of the oral cavity insertion instrument 3 will be described below.

As described above, the oral cavity insertion instrument 3 is inserted into an oral cavity of a subject patient. Once the oral cavity insertion instrument 3 is used, it will be discarded or sterilized and reused.

As shown in FIG. 8, the oral cavity insertion instrument 3 includes a cover member 31, a tongue depressor disposed adjacent to the cover member 31, and an attachment unit 33. The scope portion 23 of the monitor device 2 is inserted into the cover member 31. The tongue depressor 32 is in the form of an elongated plate. The attachment unit 33 is used to attach the oral cavity insertion instrument 3 (the cover member 31) to the monitor device 2. Constituent material of the oral cavity insertion instrument 3 is not limited to a specific one. For example, various polymeric materials such as polycarbonate may be used for the constituent material of the oral cavity insertion instrument 3.

The cover member 31 is formed from an elongated member. As shown in FIG. 9, the cover member 31 has an upper surface 31a formed by a convex curve surface swelled upward. With this configuration, a subject patient can be released from annoyance of pain, and it is possible to avoid a situation that the oral cavity insertion instrument damages a tongue or an oral cavity of the subject patient.

As shown in FIG. 10, the width W2 of the cover member 31 is approximately constant over the entire length of the cover member 31. With this configuration, the cover member 31 can have a relatively simplified structure. Furthermore, the cover member 31 can be reduced in size (or thickness).

As shown in FIG. 8, the cover member 31 has a bore to which the scope portion 23 of the monitor device 2 is inserted. The bore 311 extends in the longitudinal direction and opens at opposite ends. The opening 311a formed on the tip end of the bore 311 is closed by a substantially colorless and transparent member 34 formed of, for example, a resin member. Thus, the cover member 31 is fluidly tightened.

The length of the bore 311 is substantially the same as that of the scope portion 23. The tip end portion 231 of the scope portion 23 is located near the opening 311a of the cover member 31 when the oral cavity insertion instrument 3 is attached to the monitor device 2 (hereinafter referred to simply as "in the attached state").

The diameter of the bore 311 is approximately constant in the longitudinal direction and is slightly larger than that of the tip end portion 231 of the scope portion 23. With this configuration, the cover member 31 is supported by the scope portion 23 so as to prevent unstableness of the cover member 31 in the attached state.

In the following description, the central axis of the bore 311 is denoted by X2. In the attached state, the central axis X2 of the bore 311 conforms to the central axis X1 of the scope portion 23.

The tongue depressor 32 is provided integrally with the cover member 31.

As shown in FIG. 10, the tongue depressor 32 has a straight flat surface. The width W1 of the tongue depressor 32 is constant over an area T other than the tip end 321. As shown in FIG. 10, the tongue depressor 32 is formed symmetrically with respect to the central axis X2. With this configuration, substantially the same forces (pressures) are applied to both sides of the central axis X1 when a tongue is depressed by the tongue depressor 32. Thus, the operability of the pharyngoscope apparatus 1 can be improved.

The width W1 of the tip end 321 of the tongue depressor 32 is larger than the width W2 of the cover member 31.

Furthermore, the tip end 321 of the tongue depressor 32 extends rightward in FIG. 10 from the tip end of the cover member 31. With this configuration, when a tongue is pressed downward (toward a mandible) by the tongue depressor 32, swelled flesh produced outside the depressed portion can be prevented. Therefore, it is possible to avoid a situation that the view of an image unit 5 of the monitor device 2 is obstructed by the swelled fresh.

As shown in FIG. 10, the tip end 321 of the tongue depressor 32 is rounded. With this configuration, a subject patient can be released from annoyance of pain, and it is possible to avoid a situation that the oral cavity insertion instrument 3 damages a tongue or an oral cavity of the subject patient.

The tip portion 321 has a semicircular shape. The diameter (width) of the semicircle is the same as the width W1 of the area T. Accordingly, the oral cavity insertion instrument 3 can be smoothly inserted into and removed from an oral cavity of a subject patient. As a result, damage to teeth, a tongue, an oral cavity, a pharynx, lips, gingival mucosa, and the like can be prevented.

As shown in FIG. 8, the tip end 321 of the tongue depressor 32 is also rounded in the thickness direction. Specifically, the tip end 321 of the tongue depressor 32 has a rounded cross-section. With this configuration, a subject patient can be released from annoyance of pain, and it is possible to avoid a situation that the oral cavity insertion instrument 3 damages a tongue or an oral cavity of the subject patient.

Furthermore, as shown in FIG. 10, the tongue depressor 32 has linear edge portions 322 and 323 extending outward from the cover member 31 in the width direction (in a direction perpendicular to the longitudinal direction). With this configuration, when a tongue is pressed downward by the tongue depressor 32, swelled flesh produced outside the depressed portion can be prevented from contacting the cover member 31. By preventing such unnecessary contact with the oral cavity insertion instrument 3, a subject patient can be released from annoyance, and it is possible to avoid a situation that the oral cavity insertion instrument damages a tongue or an oral cavity of the subject patient. Additionally, the observation can be conducted stably.

As shown in FIG. 9, each of the edge portions 322 and 323 of the tongue depressor 32 is rounded in the thickness direction. Specifically, each of the edge portions 322 and 323 has a rounded cross-section. With this configuration, a subject patient is released from annoyance of pain when a tongue is depressed by the tongue depressor 32. Furthermore, it is possible to avoid a situation that the oral cavity insertion instrument damages a tongue or an oral cavity of the subject patient.

The tongue depressor 32 has such stiffness as to substantially cause no deformation when a tongue is depressed by the tongue depressor 32. Therefore, a tongue can be depressed with a small force. Thus, burdens on an operator can be reduced.

As shown in FIG. 8, the attachment unit 33 is provided on the base end of the cover member 31. With this configuration, the cover member 31 can be readily attached to the monitor device 2 (or the joint portion 24). The attachment unit 33 includes a spread portion 331 formed integrally with the cover member 31 and a regulation portion 332 formed in a sidewall of the spread portion 331.

The spread portion 331 has a shape of a circular truncated cone. The spread portion 331 has a hollow portion 331a formed inside thereof. The hollow portion 331 communicates with the bore 311 of the cover member 31. The hollow portion 331a of the spread portion 331 is slightly larger than the base portion 241 of the joint portion 24 and is approximately similar to the base portion 241 of the joint portion 24. Accordingly, the base portion 241 can be fitted to the spread portion 331. Thus, the spread portion 331 can be readily attached to the base portion 241.

The regulation portion 332 functions to regulate movement of the oral cavity insertion instrument 3 in the direction of the central axis X in the attached state. As shown in FIG. 9, the regulation portion 332 includes a pair of notches (engagement portions) 332a and 332b formed in the sidewall of the spread portion 331.

The notch 332a extends from a base end of the spread portion 331 toward a tip end of the spread portion 331 and then turns to a circumferential direction of the spread portion 331 by about 90°. In other words, the notch 332a has an L shape. The width of the notch 332a is slightly larger than the outside diameter of the engagement pin 242 of the monitor device 2 so that the engagement pin 242 is movable within the notch 332a.

The notch 332b has the same structure as the notch 332a. Those notches 332a and 332b are formed symmetrically with respect to the central axis X2.

The oral cavity insertion instrument 3 is attached to the monitor device 2 in the following manner.

First, as shown in FIG. 11A, the oral cavity insertion instrument 3 is moved toward the monitor device body 21 along the central axis X1 so that the scope portion 23 of the monitor device 2 is inserted into the bore 311 of the cover member 31.

Then, as shown in FIG. 11B, the oral cavity insertion instrument 3 is rotated about the central axis X1 so that the notch 332a and the notch 332b are aligned with the engagement pin 242 and the engagement pin 243, respectively.

Next, as shown in FIG. 11C, the oral cavity insertion instrument 3 is moved toward the monitor device body 21 along the central axis X1 until the engagement pins 242 and 243 reach the bent portions of the notches 332a and 332b, respectively.

Thereafter, as shown in FIG. 11D, the oral cavity insertion instrument 3 is rotated about the central axis X1 until the engagement pins 242 and 243 reach the ends of the notches 332a and 332b, respectively. Thus, the oral cavity insertion instrument 3 is completely attached to the monitor device 2. In this state, the oral cavity insertion instrument 3 cannot be moved in the direction of the central axis X with respect to the monitor device 2.

In order to detach the oral cavity insertion instrument 3 from the monitor device 2, operations opposite to the above are performed.

With the attachment unit 33, the oral cavity insertion instrument 3 can be readily attached to the monitor device 2, and the oral cavity insertion instrument 3 can be prevented from moving in the direction of the central axis X. Since attachment of the oral cavity insertion instrument 3 to the monitor device 2 and regulation of movement of the oral cavity insertion instrument 3 in the direction of the central axis X can be achieved at the same time, the oral cavity insertion instrument 3 can be attached to the monitor device 2 more readily. As a matter of course, the oral cavity insertion instrument can be readily replaced with a new one.

With the pharyngoscope apparatus 1 thus constructed, an oral cavity and an oropharynx can be observed without necessity for a subject patient to open his/her mouth widely. Therefore, it is possible to effectively prevent vomiting reflex which would be caused by depressing a tongue in a state in which a mouth is opened widely. In other words, an oral cavity and an oropharynx can be observed without necessity for a subject patient to open his/her mouth widely and without annoyance even in a case where the subject patient bites the oral cavity insertion instrument 3 that has been inserted into his/her oral cavity.

Furthermore, an oral cavity and an oropharynx can be observed with an image taken by the image unit. Therefore, an area in the oral cavity that can be observed is increased. Thus, accurate observation can be achieved. Furthermore, an operator can maintain his/her posture or line of sight to be constant. Accordingly, physical burdens on the operator can be reduced.

Although an oral cavity insertion instrument and a pharyngoscope apparatus according to the present invention have been described based on the illustrated embodiment, the present invention is not limited to the illustrated embodiment. For an oral cavity insertion instrument and a pharyngoscope apparatus according to the present invention, for example, each component in the above embodiment may be replaced with any component having the same function. Further, any additional component may be added to the components described above.

Furthermore, in the above embodiment, the regulation portion is formed by the notches defined in the spread portion. However, the regulation portion is not limited to such a configuration. For example, the regulation portion may be formed by one or more grooves defined in the inner wall of the spread portion.

Finally it is also to be understood that the present disclosure relates to subject matter contained in Japanese Patent Application No. 2007-338336 (filed on Dec. 27, 2007) which is expressly incorporated herein by reference in its entirely.

What is claimed is:

1. An oral cavity insertion instrument adapted to be used by being attached to a monitor device having a long scope portion with a central axis, wherein the oral cavity insertion instrument is adapted to be inserted into an oral cavity in a state that the instrument is attached to the monitor device when used, the instrument comprising:
   a long cover member having a bore which extends in a longitudinal direction thereof, wherein the scope portion of the monitor device is adapted to be inserted into the bore for attachment, the cover member has a tip end and a base end opposite to the tip end and is linearly formed from the base end to the tip end, and the cover member has a certain width;
   a long tongue depressor formed into a flat plate shape, the tongue depressor having a first surface on which the cover member is provided along the longitudinal direction thereof and a second surface which is opposite to the first surface and adapted to contact a tongue when the tongue is depressed by the tongue depressor, the tongue depressor provided adjacent to and in contact with the cover member along the longitudinal direction of the cover member, the tongue depressor having a width greater than that of the cover member, the tongue depressor having a tip end, a base end opposite to the tip end and a pair of longitudinal side edge portions each extending outward from the cover member in a direction perpendicular to the longitudinal direction of the cover member; and
   an attachment unit configured to attach the cover member to the monitor device,
   wherein the cover member has an outer surface at an opposite side to the first surface of the tongue depressor, and when the outer surface is viewed from the longitudinal direction of the cover member, the outer surface is defined by a convex curve surface that protrudes from the first surface of the tongue depressor, and the cover member is located between the pair of longitudinal side edge portions of the tongue depressor,
   wherein the tip end of the tongue depressor extends beyond the tip end of the cover member in the longitudinal direction of the cover member, and the tip end of the tongue depressor is defined by a semicircular shape and has a diameter that is the same size as a width of the base end of the tongue depressor, and
   wherein a width of the pair of longitudinal side edge portions of the tongue depressor is constant along a longitudinal direction of the tongue depressor.

2. The oral cavity insertion instrument as recited in claim 1, wherein the tip end of the tongue depressor is defined by a rounded shape in plane view of the tongue depressor.

3. The oral cavity insertion instrument as recited in claim 1, wherein an edge of the tip end of the tongue depressor is defined by a rounded shape in its cross-section.

4. The oral cavity insertion instrument as recited in claim 1, wherein, when viewed from a cross-section thereof, an edge of each of the longitudinal side edge portions is defined by a rounded shape.

5. The oral cavity insertion instrument as recited in claim 1, wherein the tongue depressor is formed symmetrically with respect to the central axis of the scope portion in a plane view of the tongue depressor.

6. The oral cavity insertion instrument as recited in claim 1, wherein the tongue depressor has such stiffness as to substantially cause no deformation when the tongue is depressed by the tongue depressor.

7. The oral cavity insertion instrument as recited in claim 1, wherein the attachment unit is formed on the base end of the cover member.

8. The oral cavity insertion instrument as recited in claim 1, wherein the attachment unit includes a regulation portion which regulates movement of the cover member with respect to the monitor device in the longitudinal direction.

9. A pharyngoscope apparatus including a monitor device having a scope portion and an oral cavity insertion instrument defined in claim 1, wherein the scope portion is in the form of a rod shape extending in the longitudinal direction and has a tip end portion and a base end portion opposite to the tip end portion.

10. The pharyngoscope apparatus as recited in claim 9, wherein the monitor device further includes a joint portion having an engagement pin protruding therefrom,
   wherein the attachment unit of the oral cavity insertion instrument includes an L-shaped engagement portion with which the engagement pin of the joint portion engages to regulate movement of the cover member with respect to the joint portion in the longitudinal direction.

11. The pharyngoscope apparatus as recited in claim 9, wherein the monitor device further includes:
- a monitor device body connected to the base end portion of the scope portion,
- an image unit operable to take an image of an observation area in the oral cavity, and
- a display unit having a display surface, and the display unit provided on the monitor device body for displaying an image taken by the image unit on the display surface.

12. The pharyngoscope apparatus as recited in claim 11, wherein the monitor device further includes an illumination unit operable to illuminate the observation area of which image is to be taken by the image unit.

13. The pharyngoscope apparatus as recited in claim 12, wherein the image unit includes:
- an object lens provided at the tip end portion of the scope portion, and
- an image pickup device having a light-receiving surface on which the image of the observation area is focused by the object lens,
- wherein the illumination unit includes a pair of illumination portions provided at the tip end portion of the scope portion so as to be symmetric with respect to the object lens of the image unit.

14. The pharyngoscope apparatus as recited in claim 13, wherein the illumination portions are located on a line extending in a direction that is parallel to a width direction of the tongue depressor.

15. The pharyngoscope apparatus as recited in claim 11, wherein the central axis of the scope portion intersects the display surface of the display unit.

16. The pharyngoscope apparatus as recited in claim 15, wherein the display surface of the display unit has a center at a location deviated from the intersection of the display surface and the central axis of the scope portion.

17. The pharyngoscope apparatus as recited in claim 11, wherein the display surface of the display unit is inclined with respect to the central axis of the scope portion.

18. The pharyngoscope apparatus as recited in claim 11, wherein the monitor device further includes a shading portion provided on the monitor device body so as to surround a periphery of the display unit.

19. The pharyngoscope apparatus as recited in claim 11, wherein the monitor device body includes at least one finger placing portion on which a finger of an operator can be placed to hold the monitor device body.

20. The pharyngoscope apparatus as recited in claim 19, wherein the at least one finger placing portion comprises a protrusion formed at an end of the monitor device body near the scope portion.

21. The pharyngoscope apparatus as recited in claim 19, wherein the at least one finger placing portion comprises a concave portion formed on the monitor device body.

22. The pharyngoscope apparatus as recited in claim 19, wherein the monitor device body has a first surface and a second surface located at the opposite side of the first surface, wherein the at least one finger placing portion comprises:
- a first finger placing portion formed on the first surface of the monitor device body, the first finger placing portion including a protrusion formed at an end of the first surface of the monitor device body near the scope portion, and
- a second finger placing portion including a concave portion formed on a second surface of the second surface of the monitor device body.

* * * * *